United States Patent [19]

Brumley, Jr. et al.

[11] Patent Number: 5,137,613

[45] Date of Patent: Aug. 11, 1992

[54] HORIZONTAL GEL ELECTROPHORESIS APPARATUS

[75] Inventors: Robert L. Brumley, Jr.; Lloyd M. Smith, both of Madison, Wis.

[73] Assignee: Wisconsin Alumni Research Foundation, Madison, Wis.

[21] Appl. No.: 630,675

[22] Filed: Dec. 20, 1990

[51] Int. Cl.$^5$ .................. B01D 61/42; C25D 13/00
[52] U.S. Cl. ...................... 204/299 R; 204/180.1; 204/182.8
[58] Field of Search ............... 204/299 R; 264/261

[56] References Cited

U.S. PATENT DOCUMENTS

| | | | |
|---|---|---|---|
| 4,415,418 | 11/1983 | Turre et al. | 204/299 R |
| 4,588,491 | 5/1986 | Kreisher et al. | 204/299 R |
| 4,612,106 | 9/1986 | Kromer et al. | 204/299 R |
| 4,693,804 | 9/1987 | Serwer et al. | 204/182.1 |
| 4,756,809 | 7/1988 | Love et al. | 204/182.8 |
| 4,773,984 | 9/1988 | Flesher et al. | 204/299 R |
| 4,795,541 | 1/1989 | Hurd et al. | 204/299 R |
| 4,830,726 | 5/1989 | Stamato et al. | 204/299 R |
| 4,849,078 | 7/1989 | Love et al. | 204/182.8 |
| 4,865,714 | 9/1989 | Sohn et al. | 204/299 R |
| 4,909,977 | 3/1990 | Hurd et al. | 264/261 |
| 4,913,791 | 4/1990 | Hurd et al. | 204/299 R |
| 4,915,811 | 4/1990 | Yamamoto et al. | 204/299 R |
| 4,919,784 | 4/1990 | Yetman | 204/299 R |

OTHER PUBLICATIONS

Conn, E. E. et al., *Outlines of Biochemistry 5th Ed.*, ed. John Wiley & Sons, N.Y. (1987) pp. 85–91 and pp. 223–225.

Ansorge, W. And DeMaeyer, L., "Thermally Stabilized Very Thin (0.02–0.3 mm) Polyacrylamide Gels for Electrophoresis," *Journal of Chromatography*, 202: 45–53 (1980).

Van Boldrik, M., "Biological Science Presentation," Aug. 23, 1990.

Newspaper article, Feb. 21, 1988.

*Primary Examiner*—John Niebling
*Assistant Examiner*—Caroline Koestner
*Attorney, Agent, or Firm*—Quarles & Brady

[57] ABSTRACT

A horizontal electrophoresis assembly is described which is designed to utilize very thin gels of polyacrylamide. The assembly allows for water cooling of the gel during electrophoresis so that higher voltages can be applied to the gel without polymer degradation. The gel mold is made from a set of glass plates which are clamped into place defining a gel mold between them. In one embodiment, the site of field introduction is separated from the site of sample introduction so that the electric field is generally linear at the region of sample introduction.

4 Claims, 6 Drawing Sheets

HORIZONTAL GEL ELECTROPHORESIS APPARATUS

BACKGROUND OF THE INVENTION

A. Field of the Invention

The present invention relates to the preparation and use of electrophoresis gels. The invention makes use of ultra-thin slab gels for the separation of macromolecules.

B. Description of the Art

Electrophoresis is the process of separating molecules on the basis of the molecule's migration in an electric field. In an electric field, a molecule will migrate towards the pole that carries a charge opposite to the charge carried by the molecule. The charge carried by a molecule often depends upon the pH of the medium in which the molecule is migrating. A common electrophoretic procedure is to set up solutions at different pH at each end of an electric field. At a certain pH, the isoelectric point of a molecule is obtained and the molecule carries no net charge. Therefore, as the molecule crosses the pH gradient, the molecule reaches an isoelectric point and is immobile in the electric field. This procedure separates molecules according to their different isoelectric points.

Electrophoresis in a polymeric gel, such as polyacrylamide or agarose, adds two advantages to an electrophoretic system. First, the polymeric gel stabilizes the electrophoretic system against convective disturbances. Second, the polymeric gel provides a porous passageway through which the molecules travel. Since larger molecules will travel more slowly through the passageways than smaller molecules, use of a polymeric gel permits the separation of molecules by either molecular size or isoelectric point.

Electrophoresis in a polymeric gel is also often used to separate molecules only by molecular size. Some groups of molecules, such as RNA and DNA molecules, all have the same electrophoretic mobility in free solution. These groups of molecules when moved through a polymeric gel by an electric field will segregate on the basis of molecular size. Thus nucleic acids and other groups of molecules with similar isoelectric points will migrate through the gel to be segregated solely on the basis of molecular size.

A polymeric gel electrophoresis system is typically set up in the following way: A gel-forming solution is allowed to polymerize between two glass plates that are held apart on two sides by spacers. These spacers determine the thickness of the gel. Sample wells are formed by inserting a comb-shaped mold into the liquid between the glass plates at one end and allowing the liquid to polymerize around the mold. The top and bottom of the polymerized gel are in electrical contact with two buffer reservoirs. Macromolecule samples are loaded into the sample wells. An electric field is set up across the gel, and the molecules begin to separate according to their size.

The size-sorted molecules can be visualized in several ways. After electrophoresis, the gels can be bathed in a DNA-specific or protein-specific stain which renders the groups of size-sorted molecules visible to the eye. For greater sensitivity, the molecules can be radioactively labelled and the gel exposed to X-ray film. The developed X-ray film will indicate the migration positions of the labelled molecules.

Both vertical and horizontal assemblies are routinely used in gel electrophoresis. The molecules can also be detected during electrophoresis, either by means of their intrinsic absorptive or fluorescent properties, or by labelling them with a detectable chromophore or fluorophore, or by other detection methods known in the art. In a vertical apparatus, the sample wells are formed in the same plane as the gel and are loaded vertically. The wells can be as deep and wide as needed, but the thickness of the well is limited by the thickness of the gel. If ultra-thin (<0.15 mm) gels are cast, loading the sample can be troublesome.

Ultra-thin electrophoretic gels are useful because they may be electrophoresed at a higher voltage. Therefore, the electrophoretic run is faster. Ultra-thin often gels yield higher resolution. Because of their thinness, the gels are fixed for autoradiography quickly and easily.

Sample wells in a horizontal apparatus are typically formed into the thickness of the gel and are loaded vertically. The wells may be of any desired thickness and, hence, are easier to load than the wells formed in a vertical apparatus. The depth of the wells is limited by the thickness of the horizontal gel.

The use of horizontal assemblies is known in the art. For example, Hurd, et al., U.S. Pat. Nos. 4,909,977 and 4,795,591, claim such a horizontal apparatus. The sample wells of the Hurd apparatus are formed by a comb-shaped mold at the extreme end of the slab gel. The comb is placed into a slot formed between the side of the bottom tray and the edge of the top tray.

Several problems are experienced by prior horizontal electrophoresis assemblies. The comb is held in place by the pressure of the top tray, but unless the comb is held very tightly, non-uniform sample wells with exogenous gel material will be formed. Additionally, the sample well geometry is such that the electric field "turns a corner" in the area of the sample well. This non-uniform electric field geometry will cause artifactual migration in this area of the gel and may cause the samples to electrophorese aberrantly. Finally, the apparatus is suitable to cast gels of 0.15–0.3 mm thick, so there is no teaching of the special problems of ultra-thin sample well formation.

The usefulness of electrophoresis depends on the sharp resolution of sample separation. This sharp resolution depends, in part, on the manner in which the macromolecular sample migrates from the sample well. Both the sample well and the electric field influence the migration of the macromolecules. Ideally, the sample wells would have a uniform, sharply defined size and have no extraneous pieces of polymerized gel that would interfere with sample migration. Uniform well size is necessary because the separation of molecules is often compared between samples that are electrophoresed side-by-side. Extraneous material in the sample well will cause impeded migration for part of the sample. Non-uniform sample migration greatly hinders high resolution molecular separation.

The placement of the electric field relative to the sample well is important because a non-uniform field can create artifactual results. Ideally, the electric field experienced by the loaded samples would be in a plane parallel to the gel, even when the sample is in the sample well. Then the molecules would experience a uniform electric field during their entire electrophoretic separation.

What is needed is an apparatus and method for casting ultra-thin gels having sample wells with a sharply defined, uniform geometry and having sample wells positioned so that the electric field passing through the sample well is parallel to the plane of the slab gel.

SUMMARY OF THE INVENTION

The present invention is an assembly for casting a slab gel and electrophoresing macromolecules in a slab gel. The assembly includes a horizontal base, a bottom plate bearing against the base, a top plate shorter than the bottom plate, with the top plate bearing on the bottom plate, an end plate bearing on the bottom plate at the loading end of the bottom plate, with the face of the end plate positioned relative to the face of the top plate so as to leave a gap that will admit a well-forming comb, a means for sealing the outer perimeter of the bottom plate and the top and end plates, a means for spacing the bottom plate from the top and end plates, a means for biasing the end plate against the top plate through a well-forming comb, and a means for passing electric current through a polymerized gel formed in the space created between the bottom plate and the top and end plates.

The present invention is also such an assembly in which the means for passing electric current through the polymerized gel formed in the space created between the bottom plate and the top and end plates includes an electrode with electrical contact to the polymerized gel through a gap through which an electric field originates. This assembly also includes a separate gap to permit sample loading through which an electric field does not originate.

The present invention is also a method for casting electrophoretic slab gels, using either assembly described above, including the steps of introducing sufficient gel-forming liquid between the top and end plates and the bottom plate to form a slab gel, inserting a well-forming comb into the gap created between the end plate and the top plate, biasing the end plate against the top plate through the comb so that the comb is held between the end plate and the top plate in a tight fit, permitting the gel-forming liquid to set, and removing the comb.

It is an object of the present invention to provide a method and apparatus that allow high resolution separation of macromolecules.

It is another object of the present invention to provide a method and apparatus capable of forming sharply defined, uniform samples wells in ultra-thin gels.

It is another object of the present invention to provide a method and apparatus capable of positioning sample wells so that the electric field passing through the sample well is parallel to the plane of the slab gel.

Other objects, advantages and features of the present invention will become apparent from the following specification when read in conjunction with the accompanying figures.

DESCRIPTION OF THE PREFERRED EMBODIMENTS

First Embodiment

Figure 1:
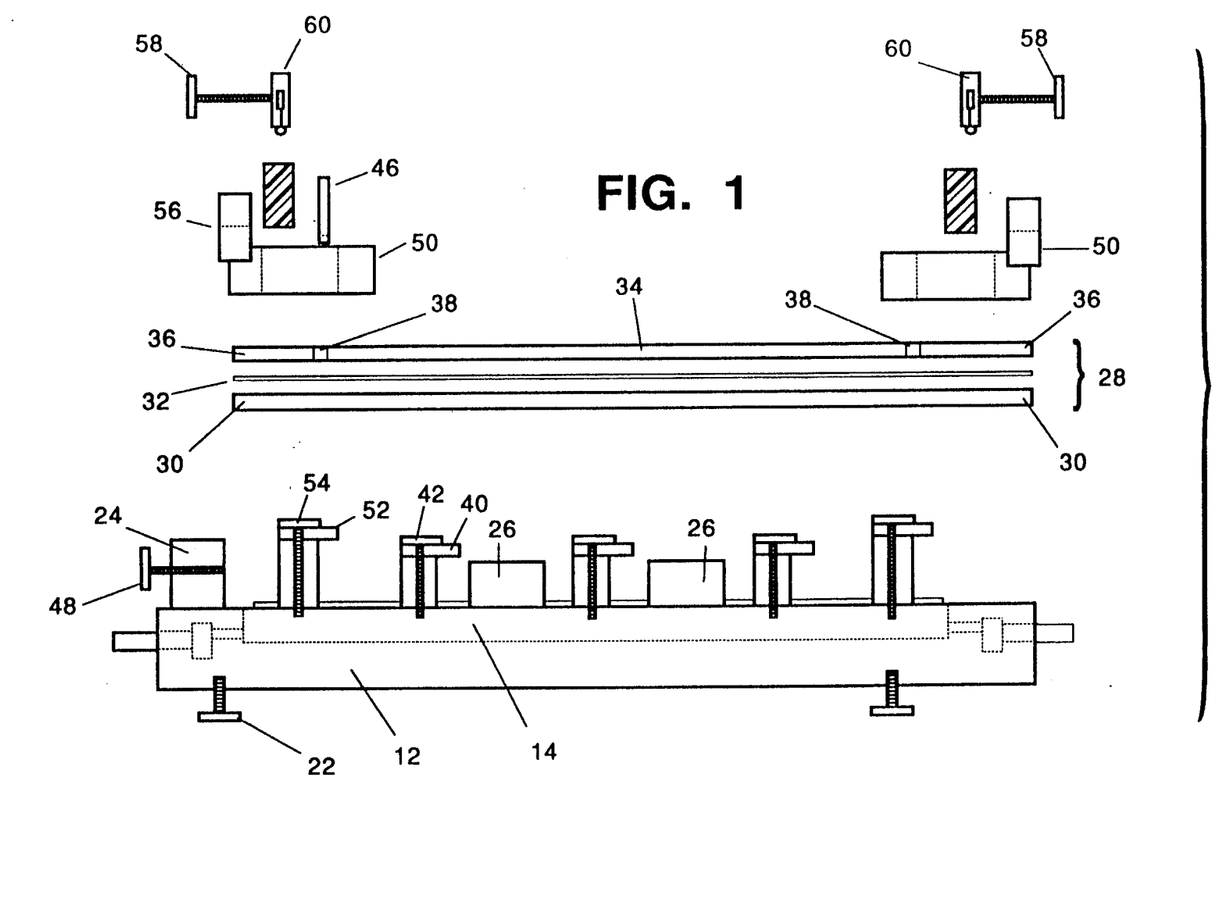
FIG. 1 is an exploded side view of a first preferred embodiment of the present invention.
Figure 2:
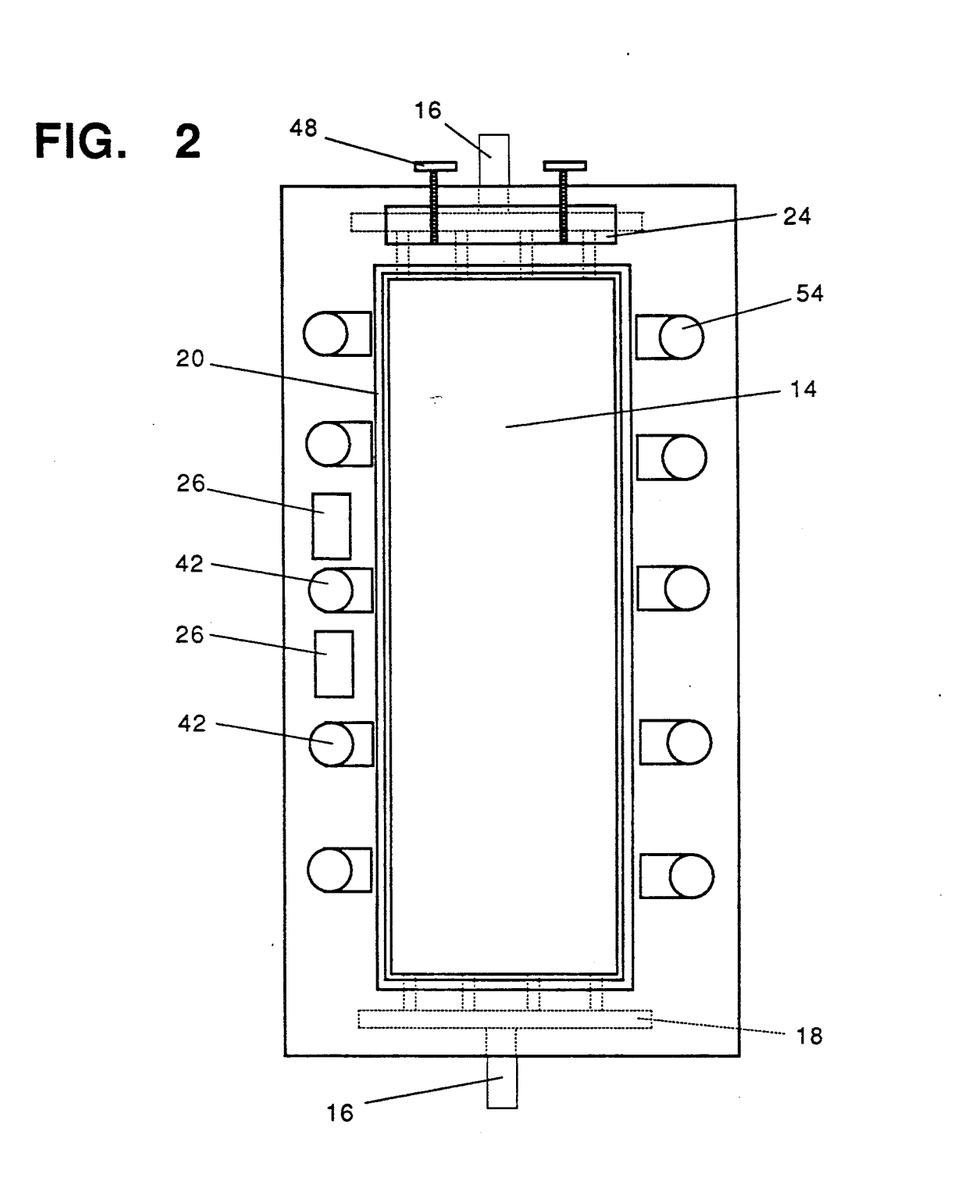
FIG. 2 is a top view of the base and elements attached to the base of the first preferred embodiment of the present invention.
Figure 3:
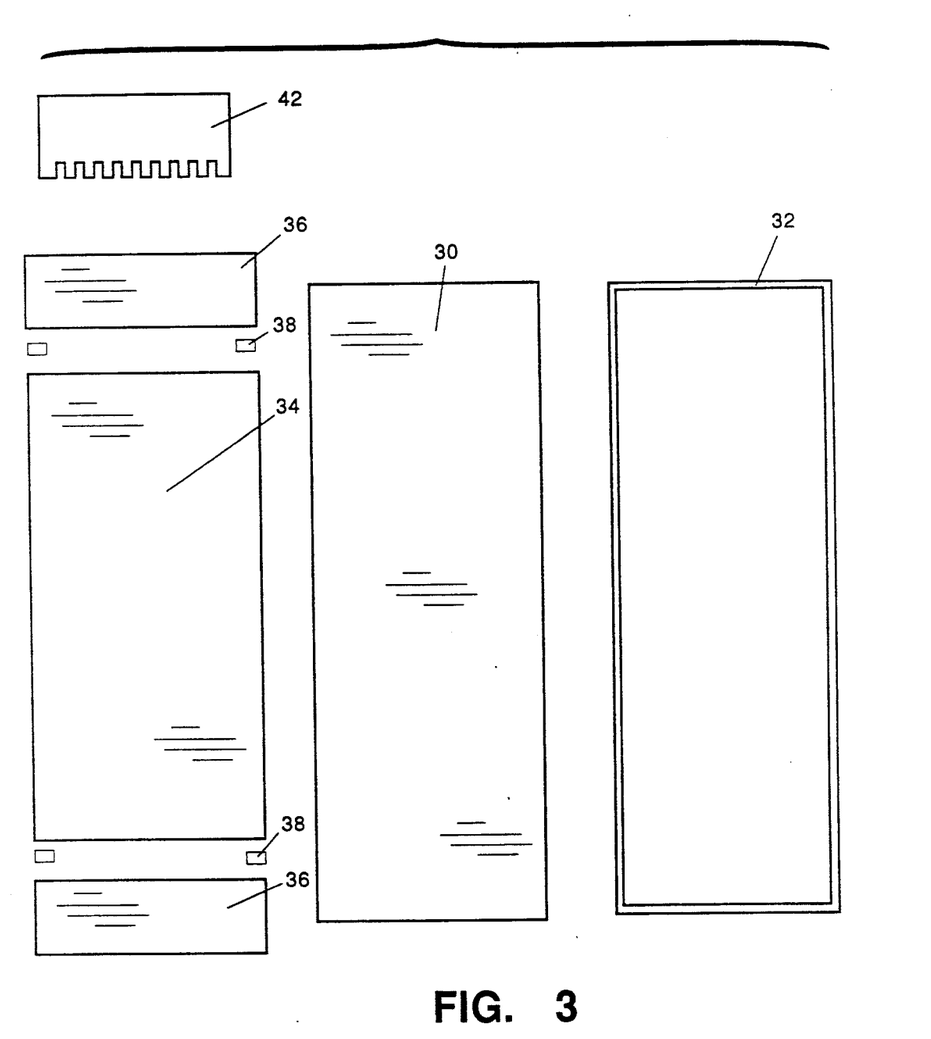
FIG. 3 is an exploded top view of the elements of the gel mold of the first embodiment of the present invention.

FIGS. 1, 2 and 3 depict the structure of the first preferred embodiment of the present invention. The following description refers to these four figures.

The apparatus of FIG. 1 includes a large rectangular horizontal base 12 which has formed in its interior a large cavity or water jacket 14. The water jacket 14 is formed as a trough, open to the top, with its three lateral sides bounded by the base 12. Coolant may flow into and out of the water jacket 14 through inlet and outlet pipes 16 connected to the water jacket 14 through manifolds 18. The inlet and outlet pipes 16 are connected by appropriate tubing to a temperature controlled water reservoir, which is also equipped with a pump (not shown) which can circulate water through the water jacket 14. An elastomeric O-Ring 20 is fitted into a groove formed in the top of the base 12 extending around the outside of the trough of the water jacket 14. Four adjustable screwed legs 22 are threaded into bores at each corner of the base 12 to support the apparatus. An end alignment bar 24 is fixed in position attached to one end of the top of the base 12. Two guide blocks 26 are attached to the top of one side of the base 12.

FIGS. 1 and 3 illustrate the parts of the gel mold 28, which is formed of a bottom plate 30, a gel gasket 32, a top plate 34, two identical end plates 36 and four identical gap formers 38. FIG. 1 shows the pieces of the gel mold 28 in the order of their assembly. The gasket 32 is placed around the outer edge of the bottom plate 30. The thickness of the gasket 32 defines the thickness of the resulting gel. Gels which will usually be less than 150 μm, and may be as thin as 25 μm, may be formed by the present invention.

In assembling the parts of the gel mold, the top plate 34 is placed on top of the gasket 32 and the end plates 36 are also placed on the gasket 32 at each end of the top plate 34. In FIG. 3, 37 and 35 indicate the faces of the end plate 36 and the top plate 34, respectively which define the edges of the sample wells. In this embodiment, the end plate 36 is approximately one-sixth the length of the top plate 34, but the relative size relationship of these parts are not critical as long as the end plate is large enough to accommodate the agarose blocks. Gap formers 38 are inserted at each corner of the top plate 34 between the ends of the top plate 34 and the end plates 36. The assembled gel mold 28 forms a water tight reservoir for gel-forming liquid. A comb 46 of the same width as the gap formers 38 can then be fit into the gap formed between the edge 35 of the top plate 34 and the edge 37 of the end plate 36.

The assembled gel mold 28 is positioned on the base 12 to abut the end alignment bar 24 and resting against the guide blocks 26. The gel mold 28 is secured tightly against the base 12 with a series of six clamps 40. The clamps 40 are placed around the sides of the base 12 and press onto the gel mold 28 by means of screws 42 threaded vertically through each clamp 40. Rotation of the screws 42 causes the top of the clamps to bear against the gel mold 28 to hold the mold 28 tightly in place against the base, thereby forming a fluid-tight seal between the lower surface of the bottom plate 30 and the O-ring 20.

At the sample-loading end of the mold 28 is an assembly for biasing the end plate 36 towards the top plate 34, against the gap formers 28 and the comb 46. In this embodiment, the assembly includes two pressure adjustment screws 48 threaded through the end alignment bar 24 which serve to apply horizontal pressure against the end plate 36.

Buffer chambers 50 are secured at either end of the mold 28 by four clamps 52. Screws 54 are threaded vertically through each clamp 52. Rotation of the screws 54 causes the top of the clamps 52 to bear against the top of the buffer chamber 50 to tightly hold the chamber against the top of the gel mold 28. An electrode holder 56 is attached to each buffer chamber 50. An adjustable screw 58 is threaded into the electrode holder 56 and secures and adjusts the carbon electrode 60. Not shown in the figures is the means for connecting a source of electric potential to the electrodes 60.

The end plates 36, top plate 34 and bottom plate 30 are preferably made of glass although other rigid transparent materials could be used such as quartz. Glass is preferred because it is electrically non-conductive and can be ground and polished to specific tolerances. If the gels are to be read optically, the glass should be one that has low fluorescence characteristics, such as fused silica glass. To ensure flatness of the glass components, optical quality glass, e.g. BK-7, Tempax, or soda-lime glass preferably polished to within 1 $\mu$m of flatness is used. The glass pieces are cut such that all sides are parallel. This parallelism is helpful for the proper alignment of the gel mold 28 on the base 12 once the components are assembled. The face 37 and 35 of the end plates 36 and the top plate 34 are polished flat to within about 5 $\mu$m. This uniform surface is helpful for the comb 46 to fit properly between the plate faces to form properly uniform wells.

The gap formers 38 and comb 46 are typically made of 0.030 inch sheet high density polyethylene. The base and attached elements may be formed of any suitable durable lightweight material, such as a dense plastic resin material.

The apparatus is used as follows. First all glass pieces are washed with a mild cleaner, rinsed with deionized water and thoroughly cleaned with three ethanol wipes. If the gels are to be fixed and dried on the bottom plate 30 after electrophoresis, the surface of the bottom glass is treated with gamma-methacryloxy-propyltrimethoxysilane which serves to bind the polyacrylamide to the glass surface. The top plate 34 may be siliconized to aid in the flow of polyacrylamide during gel pouring. Spacer surfaces may be coated with petroleum jelly to deter leakage. The gel mold 28 is assembled and positioned on the base 12 to abut the end alignment bar 24 and rest against the guide blocks 26. The screwed legs 22 positioned around the corners of the base are adjusted to provide a flat base 12. The gel mold 28 is secured onto the base with the six clamps 40. The buffer chambers 50 are clamped onto each end of the mold 28.

In this embodiment, the left-hand end of the mold 28 as viewed in FIG. 1 is the loading end. Gel-forming liquid, typically acrylamide, is introduced into the feed end buffer chamber 50 and allowed to flow into the empty space inside the gel mold 28. Enough liquid is introduced so that the liquid fills up the gel mold 28 and flows at each end into the gaps formed between the end plates 36 and the top plate 34. The gel-forming liquid is also introduced into the other chamber 50 when it has flowed across the cavity.

The well-forming comb 46 is inserted into the liquid-filled gap at the loading end. The bottom of the teeth of the comb 46 rest on the top of the bottom plate 30. The pressure adjustment screws 48 are twisted so that they bear against the end plate 36 and cause the comb 46 to be tightly squeezed between the end plate 36 and the top plate 34. Because of the tight fit of the comb 46, the leakage of gel-forming liquid around the comb 46 is strictly controlled. The wells thus formed are uniform, rectangular, sharply defined, and free of extraneous polymer that would impede electrophoresis or form irregularly shaped wells.

After the gel polymerizes, the comb 46 is carefully removed, leaving sample wells behind. The depth of these wells is determined by the length of the teeth of the comb 46. The sample wells may be formed up to the top of the top plate 34 and the end plate 36.

A small amount (approx. 1 ml.) of buffer is introduced into each buffer chamber 50. The water is also squirted with gentle pressure into the sample wells to remove residual gel-forming liquid and urea. The cooling water is begun circulating through the water jacket 14.

A 1 inch $\times$ 1 inch $\times$ 3 inch block of agarose (typically, 1.5% agarose in 1X TBE) is placed in each buffer chamber 50 with a small amount of buffer. The graphite rod electrodes 60 are positioned to be in contact with the top of the agarose blocks. Samples are loaded into the individual sample wells with a long needle syringe or pipette.

Voltage is applied across the electrophoretic slab gel, i.e. between the electrodes 60, in a short burst, typically 5000 volts for 6 seconds. During this short pulse, some of the sample moves into the slab gel. The voltage supply is turned off, and the sample wells are rinsed of excess sample. Electrophoretic resolution is improved because the migration of sample into the wells has been defined. After the wells are completely flushed, voltage is once again applied across the slab gel and the samples are electrophoresed for the desired period of time.

During electrophoresis, the gel temperature is continuously regulated by circulating coolant through the water jacket 14 under the gel mold 28. As shown in FIG. 1, coolant in the water jacket 14 will contact directly against the bottom plate 30. Coolant is dispersed across the width of the mold 28 by the manifolds 18. Coolant water is circulated by the pump associated with the external water reservoir (not shown). Because the gel is cooled while electrophoresis is taking place, up to 200 volts/centimeter of gel may be applied. Normally voltages of this intensity cannot be used in electrophoresis due to degradation of the polymeric gel from heat build-up in the gel. The cooling effect of the water jacket 14 prevents that here. A typical electrophoretic run for DNA sequencing procedures in a 75 $\mu$m 6% acrylamide gel is performed at 5000 volts for 20 minutes.

Second Embodiment

Figure 4:
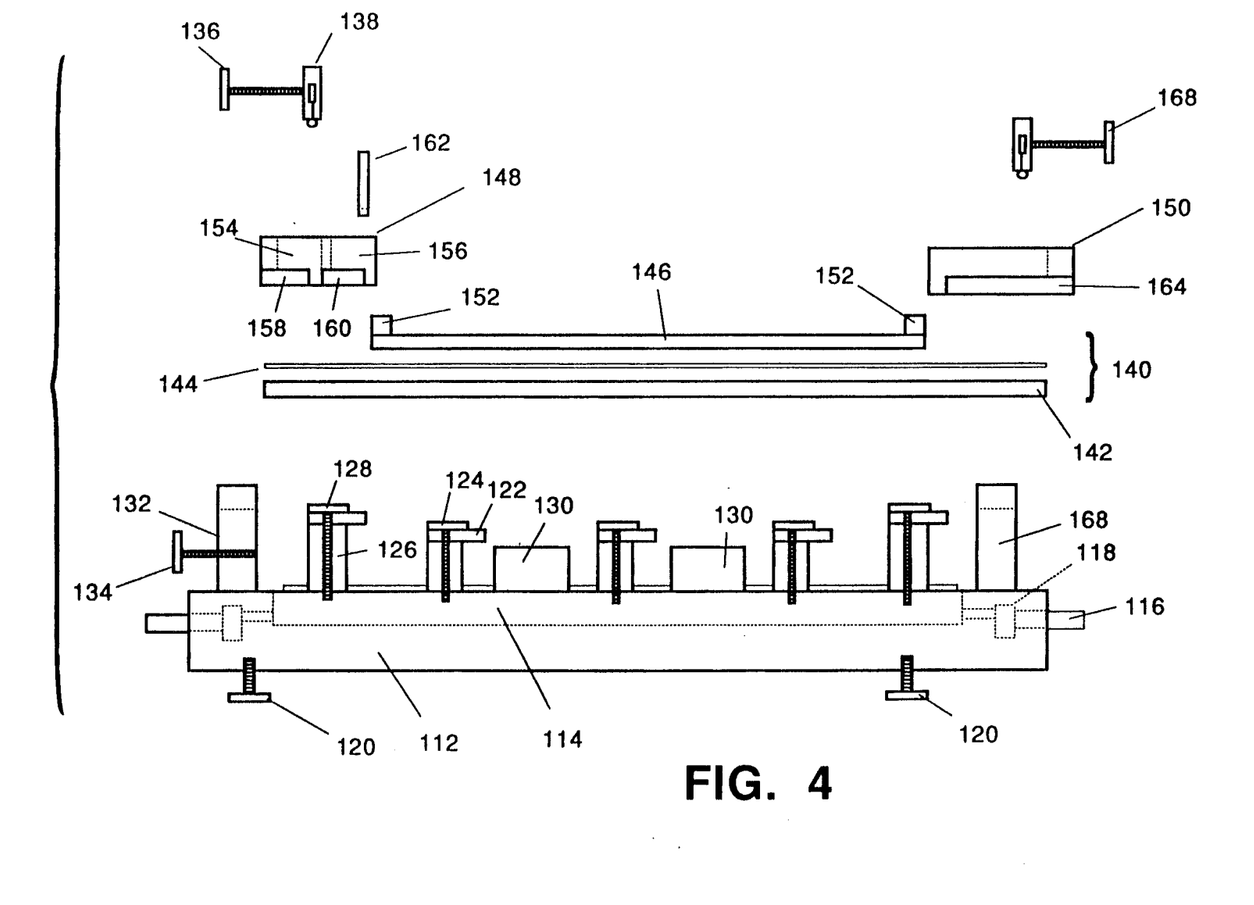
FIG. 4 is an exploded side view of the second preferred embodiment of the present invention.
Figure 5:
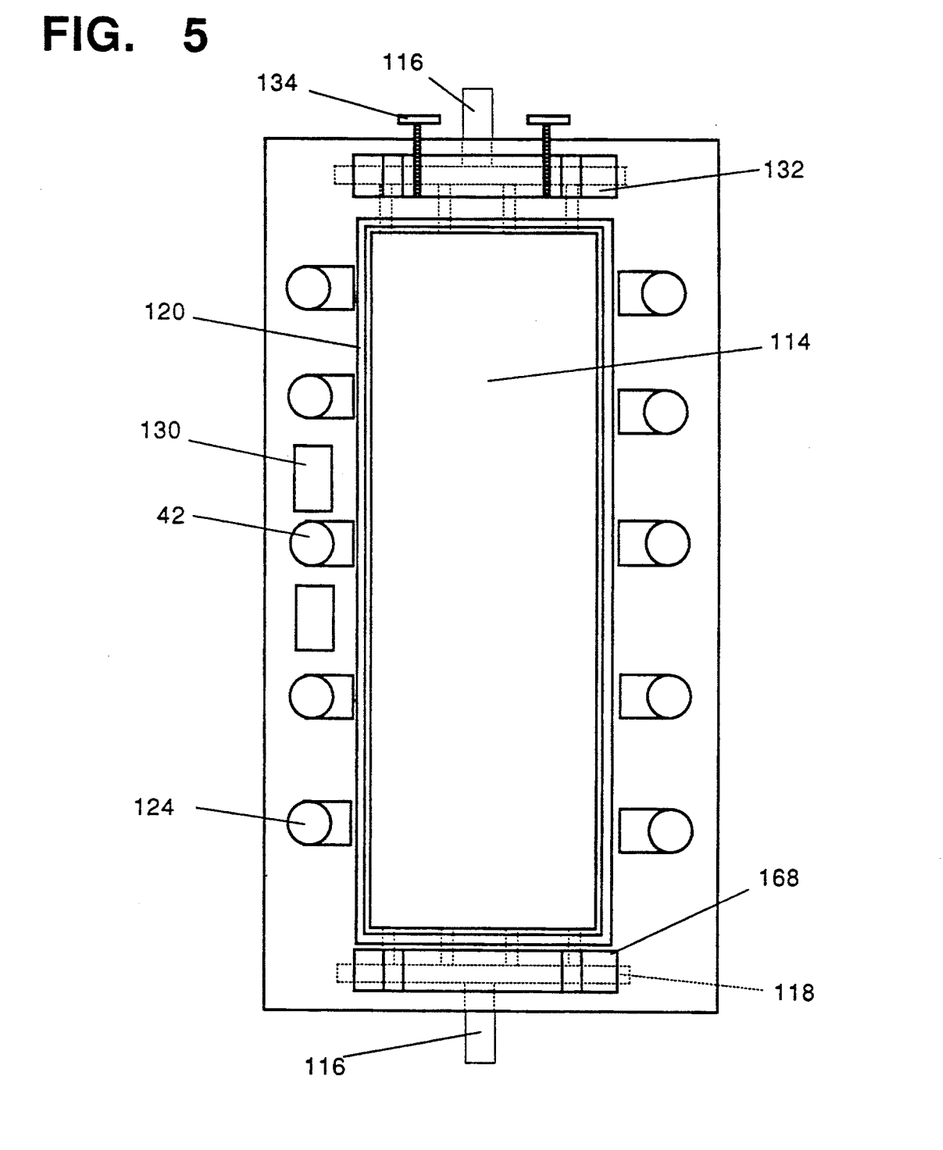
FIG. 5 is a top view of the base and elements attached to the base of the second preferred embodiment of the present invention.
Figure 6:
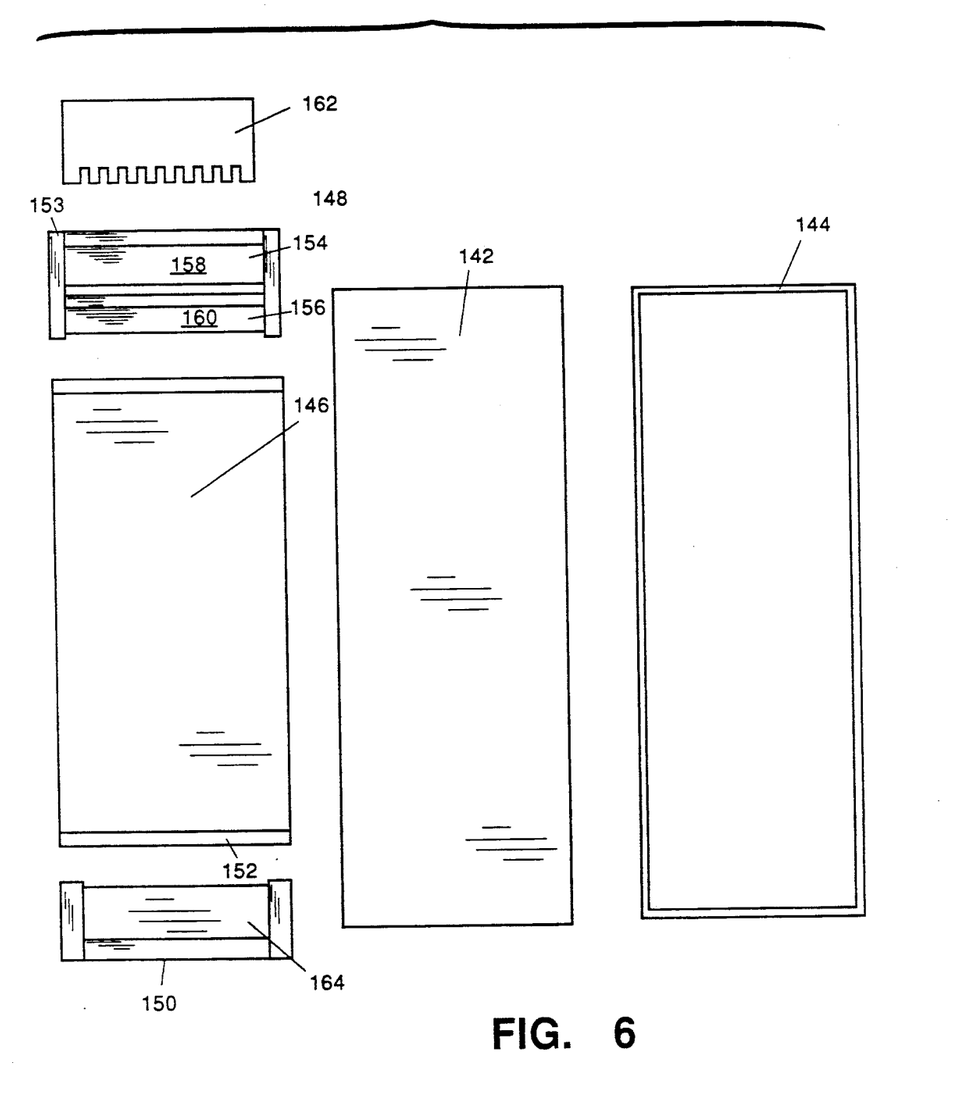
FIG. 6 is an exploded top view of the elements of the gel mold of the second preferred embodiment of the present invention.

FIGS. 4, 5 and 6 depict the structure of the second preferred embodiment of the present invention. The following description refers to FIGS. 4, 5 and 6.

A horizontal base 112, a water jacket 114, a coolant inlet and outlet pipes 116, and inlet and outlet manifolds 118, height adjustment screw legs 120, mold clamps 122, mold clamp screws 124, buffer chamber clamps 126, buffer chamber clamp screws 128, and guide blocks 130 are identical structurally and functionally with those of the first embodiment and thus need not be described again in detail. An end alignment bar 132 is attached to the loading end of the base 112. This end alignment bar 132 has two pressure adjustment screws 134 threaded through it, as in the first embodiment. The end adjustment bar in this embodiment also holds the electrode assembly adjustment screws 136 which adjusts the position of the graphite electrode 138.

The gel mold 140 in this embodiment is defined by the surfaces of a bottom plate 142, and gasket 144, a top plate 146, a sample well and electrode assembly 148 and an electrode assembly chamber 150. FIGS. 4 and 6 depict these elements. The thickness of the gasket 144 defines the thickness of the gel. Gels as thin as 25 μm may be formed using this embodiment. The bottom plate 142 and the gasket 144 are identical structurally and functionally with those of the first embodiment. The top plate 146 has a lateral bar 152 attached to its top, at both its ends.

The sample well and electrode assembly 148, depicted in FIGS. 4 and 6, includes an assembly frame 153 which borders the assembly and divides the interior of the assembly into two open-topped chambers, a field transfer chamber 154 and a sample chamber 156. The field transfer chamber 154 has a plate 158 partially extending across its bottom. The plate 158 is positioned so that a gap at its front end permits electrical contact between material contained within the chamber 154 and the polymerized gel. The sample chamber 156, which is also open toward its front side, also has a plate 160 extending part of the way across its bottom. When the gel mold 140 is assembled, the lateral bar 152 forms the front side of the sample chamber. The plate 160 is positioned to leave a gap between the bottom of the sample chamber 156 and the edge top glass 146. This gap is the same width as the well-forming comb 162. The edge of the plate 160 and of the top glass 146 are polished to within 5 micrometers to provide accurate wells. A partition 164 separates the field transfer chamber 154 and the sample chamber 156. Note that the side edges of the sample well assembly frame 153 extend forwardly past the plate 160, or downward as illustrated in FIG. 5. The distance that the edges of the assembly frame 153 extends past the plate 160 is the width of the comb 162.

The electrode chamber 150 also has a plate 165 as its bottom. This plate 165 is positioned to leave a small gap for electrical contact and field transfer to the polymerized gel from the buffer chamber 150. An electrode assembly support 168 is attached to the base 112 at the non-loading end of the gel and holds the electrode adjustment screws 136 which support and position the electrode 138 at the non-loading end of the base 112.

Elements of the second embodiment are typically constructed of similar materials as in the first embodiment. The bottom plate 142, top plate 146 and the plates 158, 160 and 164 are preferably formed of glass. The frame of the sample well assembly 148 and buffer chamber 150 may be made of other materials, such as a durable plastic resin.

The second embodiment functions as follows. The top surface of the bottom plate 142 is treated for adhesion to the gel. The gel mold 140 is then assembled and positioned onto the base to fit against the guide blocks 130 and the end alignment bar 132, and is then secured onto the base 112 by the mold clamps 122 and the buffer chamber clamps 126. Height adjustment screw legs 120 are used to position the base 112 so that it is perfectly horizontal.

Gel-forming liquid is introduced into any of the gaps in the gel mold 140, such as the gap in front of the plate 158 in the field transfer chamber 154. Sufficient liquid is introduced to fill the mold 140 and the gaps. The comb 162 is inserted into the gap in the sample chamber 156 of the sample well assembly 148 and the pressure adjustment screws 134 are twisted so that the sample well assembly 148 is pressed against the top glass 146 with the comb 162 in place. The comb 162 is thus held tightly between the plate 160 that forms the bottom of the open-sided chamber and the top glass 146. This tight fit results in sharply defined, uniform wells.

The gel is allowed to polymerize, the pressure adjustment screws 134 are loosened, and the comb is carefully removed. The wells are flushed with distilled water. Excess water is wiped away from the plate 160 and the bottom of the sample chamber 156 with a tissue. A minute amount of water is left in each sample well.

In this embodiment, the electrodes are contacted directly to an extension of the gel itself. After the gel-forming material has polymerized in the gel mold, a second batch of gel-forming material is formulated. While a typical polyacrylamide gel is made by mixing 10 ml 6% polyacrylamide with 50 microliters of 10% APS and 5 microliters TEMED, the second batch of 10 ml of gel-forming solution material is made with three times the concentration of TEMED initiator. This second batch of gel-forming material is poured into the charge transfer chambers 154 and 150, and allowed to polymerize for approximately two hours. The result is a gel that extends continuously from one charge transfer chamber to the other through the gel mold 140. The electrodes impose the field on the gel by being placed in direct physical contact with the gels formed in the charge transfer chambers Thus no buffer or other intermediary material is required to transfer the electric field into the gel.

In this embodiment, the electrical contact takes place through the field transfer chamber 154 and not through the sample wells. The electric field travels from the electrodes, through the gel in the charge transfer chambers, through the gaps formed adjacent plates 160 and 165 and then horizontally through the gel. Thus although the path of the electric field is bent in the chambers and in passing through the gaps, in the entire length of the gel in which the electrophoresis is performed, the field is linearly horizontal. Also, when the electric field passes through the sample wells, it is in a linear plane approximately parallel to the slab gel. Samples electrophoresed in this manner will not suffer from a period of artifactual migration that occurs when the electric field "turns a corner," as it does in the first embodiment and many prior art horizontal gel devices. This improved electric field geometry results in sharper, more uniform sample resolution and separation.

It has been discovered that the electrophoresis apparatus constructed in accordance with the present invention is capable of accurately, efficiently and quickly resolving DNA samples, particularly for DNA sequencing procedures The provision for the base plate 142, which is continuously cooled on its underside, enables a thin polyacrylamide gel to be made and used without temperature build-up. Because higher voltages can be used, the separation of DNA strands can be accomplished more rapidly than previously possible, with no loss of accuracy or resolution.

These two embodiments do not represent the full scope of the invention. The invention may be employed in other embodiments, as well. Therefore, reference should be made to the claims for interpreting the breadth of the invention.

We claim:

1. An assembly for casting a slab gel and electrophoresing macromolecules in a slab gel, comprising:
    (a) a horizontal base;
    (b) a bottom plate bearing against said base;
    (c) a top plate shorter than said bottom plate, said top plate bearing on said bottom plate, said top having a face;
    (d) a sample-well assembly including a well-forming gap formed therein bearing on said bottom plate at the loading end of said bottom plate, said sample-well assembly having a face, the face of the sample-well assembly positioned horizontally adjacent to the face of said top plate so that the well-forming gap is oriented toward the top plate;
    (e) means for sealing the outer perimeter of said bottom plate, said top plate and said sample-well assembly together, said sealing means also spacing the bottom plate from the top plate and the sample-well assembly to form a gel mold, the gel mold adapted so that a polymerized gel may be formed therein;
    (f) means for mechanically biasing said sample-well assembly against said top plate leaving the well-forming gap therebetween adapted to permit insertion of a well-forming comb so that samples may be loaded into the polymerized gel through the well-forming gap; and
    (g) a first electrode and second electrode for passing electric current through the polymerized gel formed in the gel mold, the the first and second electrode being located at opposite ends of the gel mold and connected to apply the electric field through the gel mold, the electrode located at the same end of the gel mold as the well-forming assembly being electrically connected to the gel mold at a point different from the well-forming gap such that the electric field created in the polymerized gel is approximately horizontal through the well-forming gap.

2. The assembly of claim 1, additionally comprising means for cooling said base during electrophoresis.

3. The assembly of claim 1, wherein said sealing means and said spacing means is a gasket.

4. The assembly of claim 1, wherein said biasing means comprise a screw threaded through an end alignment bar.

* * * * *

UNITED STATES PATENT AND TRADEMARK OFFICE
CERTIFICATE OF CORRECTION

PATENT NO. : 5,137,613

DATED : August 11, 1992

INVENTOR(S) : Robert L. Brumley, Jr. and Lloyd M. Smith

It is certified that error appears in the above-identified patent and that said Letters Patent is hereby corrected as shown below:

Column 1, after the title insert:

-- This invention was made with United States government support awarded by the National Institute of Health (NIH), Grant # 1R01GM42366-01 and the National Science Foundation (NSF), DIR-8957582. The United States Government has certain rights in this invention.--

Signed and Sealed this

Fifteenth Day of February, 1994

Attest:

BRUCE LEHMAN

Attesting Officer

Commissioner of Patents and Trademarks